United States Patent
Zisapel et al.

(10) Patent No.: US 7,332,177 B1
(45) Date of Patent: Feb. 19, 2008

(54) METHOD AND FORMULATION FOR TREATING RESISTANCE TO ANTIHYPERTENSIVES AND RELATED CONDITIONS

(75) Inventors: Nava Zisapel, Tel Aviv (IL); Moshe Laudon, Kfar Saba (IL)

(73) Assignee: Neurim Pharmaceuticals (1991) Ltd., Tel Aviv (IL)

( * ) Notice: Subject to any disclaimer, the term of this patent is extended or adjusted under 35 U.S.C. 154(b) by 0 days.

(21) Appl. No.: 10/169,467

(22) PCT Filed: Jan. 5, 2000

(86) PCT No.: PCT/IL00/00009

§ 371 (c)(1),
(2), (4) Date: Sep. 20, 2002

(87) PCT Pub. No.: WO01/49286

PCT Pub. Date: Jul. 12, 2001

(51) Int. Cl.
*A61F 2/02* (2006.01)
*A61F 6/06* (2006.01)
*A61F 13/02* (2006.01)
*A61K 9/48* (2006.01)
*A61K 9/20* (2006.01)

(52) U.S. Cl. .............. 424/423; 424/427; 424/430; 424/435; 424/436; 424/451; 424/464

(58) Field of Classification Search .......... 424/451, 424/464, 436, 423, 427, 430, 452, 457, 465, 424/468

See application file for complete search history.

(56) References Cited

U.S. PATENT DOCUMENTS 5,508,039 A 4/1996 Yates et al.
5,700,828 A 12/1997 Federowicz et al.
5,849,338 A * 12/1998 Richardson et al. ........ 424/682

FOREIGN PATENT DOCUMENTS

EP 0 518 468 A1 12/1992

OTHER PUBLICATIONS

Arangino, Serenella et al., "Effects of Melatonin on Vascular Reactivity, Catecholamine Levels, and Blood Pressure in Healthy Men," *American Journal of Cardiology*, May 1, 1999, pp. 1417-1419, vol. 83(9).
Birau, Nikolaus et al., "Hypotensive Effect of Melatonin in Essential Hypertension," *IRCS Medical Science*. 1981, p. 906, vol. 9, No. 10.
Brugger, P. et al., "Impaired nocturnal secretion of melatonin in coronary heart disease," *The Lancet*, Jun. 3, 1995, p. 1408, vol. 345.
Lusardi, P. et al. "Effect of bedtime melatonin ingestion on blood pressure or normotensive subjects," *Blood Pressure Monitoring*, 1997, pp. 99-103, vol. 2(2).
Zaslavskaia, RM et al., "Comparative study of the effectiveness of Cozaar monotherapy and Cozaar and melatonin combined therapy in aged patients with hypertension," *Klin Med (Mosk)*, 1998, pp. 49-51, vol. 76(12). ABSTRACT PMID: 10067294.
Zaslavskaia, RM et al., "Effects of melatonin alone and in combination with aceten on chronostructure of diurnal hemodynamic rhythms in patients with hypertension stage II," *Ter Arkh.*, 1999, pp. 21-24, vol. 71(12). ABSTRACT PMID 10647194.

* cited by examiner

*Primary Examiner*—Carlos A Azpuru
(74) *Attorney, Agent, or Firm*—Rothwell, Figg, Ernst & Manbeck

(57) ABSTRACT

A method for the prevention or treatment of symptoms of hypertension in a patient who is resistant to antihypertensive effects of an antihypertensive compound administered in the absence of melatonin comprises administering to said patient melatonin in an amount effective to ameliorate or prevent symptoms of hypertension in said patient.

8 Claims, No Drawings

METHOD AND FORMULATION FOR TREATING RESISTANCE TO ANTIHYPERTENSIVES AND RELATED CONDITIONS

BACKGROUND OF THE INVENTION

1. Field of the Invention

The present invention relates to a method and pharmaceutical formulation for treating a patient who is resistant to the antihypertensive effect of an antihypertensive compound in absence of melatonin, a method for lowering nocturnal blood pressure in patients who have an abnormal rhythm in blood pressure in the absence or presence of an antihypertensive compound, a method for lowering cortisol levels and protecting from cardiovascular events, and use of melatonin in the manufacture of medicaments for the stated purposes.

2. Description of Related Art

There is a daily variation in blood pressure (circadian blood pressure rhythm) which is characterized by a nocturnal fall and a diurnal rise. The normal pattern of circadian blood pressure rhythm is reversed in elderly people and in those with Cushing's syndrome, those undergoing glucocorticoid treatment, those with hyperthyroidism, central and/or peripheral autonomic dysfunction (Shy-Drager syndrome, tetraplegia, diabetic or uremic neuropathy etc.), chronic renal failure, renal or cardiac transplantation, congestive heart failure, eclampsia, sleep apnea syndrome, malignant hypertension, systemic atherosclerosis, accelerated hypertensive organ damage (Imai, Abe et al, Journal of hypertension (supplement) 8:S125-132, 1990) and fatal familial insomnia (Portaluppi, Cortelli et al. Hypertension 23:569-576, 1994). A less-than-normal decline in nocturnal blood pressure is seen in some hypertensive patients despite treatment with antihypertensive drugs. A less-than-normal decline in nocturnal blood pressure has been associated with excessive cardiovascular complications in hypertensive patients. Patients with impaired nocturnal blood pressure reduction (nondippers) are at increased risk of developing target organ damage (1-4) and nondipper women have been shown to develop more cardiovascular events (5) than their dipper counterparts. The mechanism of the normal fall of blood pressure during sleep and the pathophysiological mechanisms responsible for lack of nocturnal fall in blood pressure remain to be fully elucidated.

Glucocorticoid hormones play a critical role in a variety of bodily functions. In the basal state, glucocorticoids exert a permissive effect on diverse body functions such as maintenance of blood pressure, euglycemia, and electrolyte and water hemostasis. In humans, cortisol is essential for life. Normally, cortisol secretion from the adrenal gland is rhythmic, with maximal blood levels in the early morning hours, and a decline to half of the peak value in the afternoon. During stress, excretion of cortisol is greatly increased to cope with serious whole body insult. However, sustained elevation of cortisol in circulation has detrimental effects on the immune system and on the ability of the body to cope with stress and disease. Most importantly, corticosteroids can provoke a neurodegenerative process in the hippocampus leading to impaired memory and cognitive functions. Prolonged exposure of the brain to corticosteroids makes it more vulnerable to degeneration induced by ischemia and epilepsy (McEwen, Annals of the New York Academy of Science, 1994, 746: 145-154). With aging, the basal secretion of cortisol increases by unknown mechanisms and its peak occurs earlier in the morning than in young adults (Moreley and Korenman, eds., Blackwell Scientific Publications, 1992, pp. 70-91). In addition, nocturnal cortisol levels have been found to be higher in coronary patients than aged-matched healthy subjects (Brugger and Herold, Biological Rhythm Research, 1995, 26: 373). There is an association between hypertension and high urine cortisol values (Lichtenfeld, Hunt et al, Hypertension, 31:569-74, 1998), oral cortisol increases blood pressure in a dose dependent manner (Kelly, Mangos et al, Clin Exp Pharmacol Physiol Suppl 25.S51-6, 1998). It has not been previously suggested that there is an association between the high cortisol levels and the absence of nocturnal dip in blood pressure.

Melatonin, the hormone secreted at night from the pineal gland, reaches its peak levels before the onset of the cortisol peak in humans. The production of melatonin declines with age. Also, nocturnal melatonin levels are lower in coronary patients than in healthy aged-matched individuals. However, it has not been suggested that melatonin affects cortisol secretion under normal conditions.

Cardiovascular Effects of Conventional Release Melatonin

Melatonin, the hormone of the pineal gland, is normally secreted at night and plays a role in the biologic regulation of circadian rhythms, including sleep (Brzezinski, N Engl J Med 1997; 336: 186-195, Penev and Zee, Ann Neurol 1997; 42: 545-553). Vasorelaxing action of melatonin (at high concentrations 10-1000 μM) has been observed in rabbit aorta in vitro (Satake et al., Gen. Pharmacol., 1991, 22: 219-221, and 22:1127-1133).

Rodent studies indicate the presence of melatonin receptors in some arterial vessels and it's ability to modulate rat vascular smooth muscle tone (Capsoni et al, Neuroreport 1995; 6: 1346-1348, Mahle et al, J Biol Rhythms 1997; 12: 690-696). This modulation may be manifested as vasodilatation or vasoconstriction depending on the animal species.

The effects of melatonin on blood pressure and on the human cardiovascular system is complex (Lusardi et al, Blood Press Monit 1997; 2: 99-103, Cagnacci et al, 1998; 274: 335-338, Arangino et al, Am J Cardiol 1999; 83: 1417-1419; Terzolo at al. J. Pineal Research, 1990, 9: 113-124). Bedtime melatonin ingestion (5 mg) for 4 weeks to young normotensive subjects caused a decrease in systolic blood pressure throughout the 24 h period, a decrease in diastolic blood pressure limited to the second half of the night, a slight lowering of the heart rate during the diurnal hours, and an acceleration during the second half of the night (Lusardi et al, Blood Press Monit 1997; 2: 99-103). The daytime administration of melatonin (1 mg) to young women or men reduced the systolic and diastolic blood pressure within 90 min after administration Cagnacci et al, 1998; 274: 335-338; Arangino et al, Am J Cardiol 1999; 83: 1417-1419)). The administration of melatonin at 08:00 to aged postmenopausal women surprisingly increases their cortisol levels (Cagnacci, Soldani and Yen, L Pineal Res, 22:81-5, 1997).

The effects of long-term (2 months), low dose (2 mg/os daily), time specified (18:00 h) melatonin administration on endocrine and cardiovascular variables in adult men have also been studied by Terzolo at al. (J. Pineal Research, 1990, 9: 113-124). After treatment, a marked elevation of mean serum melatonin levels were recorded, with a significant advance of its circadian rhythm. The 24 h patterns of cortisol and testosterone displayed an anticipation of the morning acrophases at about 1.5 h (not significant) for cortisol and 3 h (significant) for testosterone. Prolactin pattern was unchanged as well as serum levels of triiodothyronine and thyroxine. Likewise, the response of luteinizing hormone (LH), follicle stimulating hormone (FSH), prolactin, thyroid stimulation hormone (TSH) cortisol, adrenocorticotrophin (ACTH) and aldosterone to a stimulation test with gonadotropin releasing hormone (GNRH) thyrotropin releasing hormone (TRH), adrenocorticotrophin (ACTH) and testosterone to human chorionic gonadotrophin (HCG) were also unaffected. The circadian organization of the cardiovascular variables, i.e. systolic and diastolic blood pressure, heart rate, did not show any changes after melatonin treatment.

It is an object of the present invention to the lower cortisol level in humans and particularly to defer the peak of cortisol in the human cortisol profile. It is a further object of the invention to lower the blood pressure of a patient who is resistant to the antihypertensive effect of an antihypertensive compound in absence of melatonin, and especially to lower the nocturnal blood pressure in non-dippers. It is believed that these objects will potentially contribute to decrease in blood pressure, prevention of ischemic attacks and provide prophylactic protection against the detrimental effects of ischemia on the heart. Other objects of the invention will be apparent from the description which follows.

In U.S. Pat. No. 5,700,828, there is described a method for treating or minimizing anoxic or ischemic brain injuries, by administering melatonin to a mammal suffering from an anoxic or ischemic insult, this being defined as a trauma that causes a lack of blood flow to the brain and/or a lack of oxygen to the brain. This patent does not suggest that melatonin might prevent or ameliorate the anoxic or ischemic insult, per se.

In U.S. Pat. No. 5,849,338, filed Aug. 26, 1997, there is described a unit dosage form for treating vasoconstriction and physiological conditions giving rise to it, comprising, in brief, Mg, vitamins C and E, folic acid, Se and melatonin. Melatonin is included only because of certain of its properties which were known at the filing date and which are described in this patent.

The entire contents of these U.S. patents are incorporated by reference herein.

SUMMARY OF THE INVENTION

The above objects may be achieved by the present invention, which in one aspect, provides a pharmaceutical formulation which comprises, in addition to at least one carrier, diluent or adjuvant:

melatonin in an amount effective to ameliorate or prevent symptoms of hypertension developing in a patient who is resistant to the antihypertensive effect of an antihypertensive compound administered in absence of melatonin, and at least one antihypertensive compound in an amount effective to exert an antihypertensive effect in presence of melatonin, in a patient requiring such treatment.

The present invention also provides use of melatonin in the manufacture of a medicament for the prevention or treatment of symptoms of hypertension in a patient who is resistant to the antihypertensive effect of an antihypertensive compound administered in absence of melatonin, as well as a method for the prevention or treatment of symptoms of hypertension in a patient who is resistant to the antihypertensive effect of an antihypertensive compound administered in absence of melatonin, which comprises administering melatonin to such patient, in an amount effective to ameliorate or prevent symptoms of hypertension developing in the patient.

According to another aspect, the invention provides use of melatonin in the manufacture of a medicament for imparting in a patient at least one effect selected from improvement in mood and daytime vigilance, postponement of the peak level of cortisol in the patient and potential prophylactic protection against the detrimental effects of ischemia on the heart, the medicament being a pharmaceutical formulation which comprises melatonin in an amount effective to impart at least one of the above-stated effects.

According to still another aspect, the invention provides a method for imparting in a patient at least one effect selected from improvement in mood and daytime vigilance, postponement of the peak level of cortisol in the patient and potential prophylactic protection against the detrimental effects of ischemia on the heart, which comprises administering to the patient melatonin in an amount and in a manner effective to achieve said at least one effect.

The expression "improvement in mood" in the present context is intended to connote avoidance of mood depression which may be associated with administration of melatonin in conventional form, i.e. not in controlled release form.

Surprisingly, administration of melatonin to humans appears to lower excretions rates and diurnal variations. Also, there is a difference in this respect between controlled- and regular-release melatonin in that the controlled release form is able to change and delay the diurnal profile of cortisol whereas the regular form just suppresses but does not shift significantly the time of the peak.

DETAILED DESCRIPTION OF THE INVENTION

The medicament/pharmaceutical formulation may be administered in any convenient form, such as one adapted for oral, rectal, parenteral or transdermal administration. It may be e.g. in unit dosage form. In a particular embodiment, the melatonin is in the form of a controlled release formulation, wherein the melatonin is preferably released at a predetermined controlled rate.

The controlled release formulation can be in particulate form comprising coated particles and the desired controlled release properties can be achieved by at least one of the following features: (a) variation in the particle size of the melatonin; (b) use of at least two coating materials which dissolve at different rates in the human body; or (c) variation in the thickness of at least one coating material, whereby particulate melatonin is coated with different thicknesses of the coating material(s) which dissolve at different rates in the human body.

The at least one carrier, diluent or adjuvant may, for example, include at least one acrylic resin.

The amount of melatonin presently contemplated for use in preventing or treating hypertension will be the amount found to be effective for this purpose, presently believed to be, in the case of oral administration, more than 0.5 mg and no more than 100 mg daily, e.g. 0.5-50 mg, preferably 2.5-20 mg, and for parenteral or transdermal administration, between 0.1 and 50 mg. In accordance with the invention, an effective amount of melatonin may be formulated e.g. together with an effective dosage of a antihypertensive drug. The present medicament/pharmaceutical formulation may comprise also at least one melatonin receptor modifier and/or melatonin profile modifier.

Once the concept of the present invention for treatment or prevention of hypertension using melatonin is known according to the present invention, no inventive skill would be required to ascertain the range of effective amounts of melatonin for the present purpose, for various routes of administration. Where the pharmaceutical formulation includes at least one antihypertensive agent, this may for example be selected from Diltiazem, Captopril, Atenolol, Benazepril, Enalapril, Valsartan, Metoprolol, Terazosin, Prazosin, Minoxidil, Clonidine, Ramipril and pharmaceutically acceptable salts thereof. The daily dosage rates for oral administration of the exemplified hypertensive compounds, is shown in the following table:

TABLE 1

Antihypertensive Compounds

| Compound | Daily Dosage (mg) | |
|---|---|---|
|  | possible | usual |
| Diltiazem HCl | 180-300 | 240 |
| Captopril | 12.5-50 | 12.5 |
| Atenolol | 100 | 100 |
| Benazepril HCl | 5-20 | 10 |
| Enalapril Maleate | 5-20 | 10 |
| Valsartan | 80-160 | 80 |
| Metoprolol tartarate | 95-200 | 100 |
| Terazosin HCl | 1-10 | 1 |
| Prazosin HCl 4-64 | 0.5-5 | 0.5-1 |
| Minoxidil | 5 | 5 |
| Clonidine HCl | 0.15 | 0.15 |
| Ramipril | 1.25-5 | 2.5 |

The invention will be illustrated by the following Examples.

EXAMPLE 1

The following ingredients are mixed together and the mixture was compressed in a 7 mm cylindrical punch, at 2.5 tons, in order to make controlled release tablets: Captopril (12.5 mg/tablet), melatonin (5 mg/tablet), and Eudragit™ RS 100 acrylic resin carrier (Rohm Pharma) and lactose in an approximately 1:1 ratio by weight. While this formulation should be administered in accordance with a physicians instructions, it is presently contemplated that two such tablets taken two hours before bedtime would be appropriate.

EXAMPLE 2

The following ingredients are mixed together and the mixture was compressed in a 7 mm cylindrical punch, at 2.5 tons, in order to make controlled release tablets: Diltiazem (180 mg/tablet), melatonin (5 mg/tablet), and Eudragit™ RSPO acrylic resin carrier (Rohm Pharma), lactose and calcium hydrogen phosphate in an approximately 2:1:2.5 ratio by weight. While this formulation should be administered in accordance with a physicians instructions, it is presently contemplated that two such tablets taken two hours before bedtime would be appropriate.

EXPERIMENT 1

The effect of melatonin on blood pressure was determined on a trial population of 52 hypertensive and 130 normotensive elderly patients. All patients, who had been insomniacs, were diagnosed according to DSM IV. They consisted of 86 men and 96 women, age 72±9 years. In a randomized, double blind, subjects were given daily either 1, 2 or 5 mg melatonin in a controlled-release formulation (Circadin™, Neurim Pharmaceuticals, Israel), two hours before bedtime, or a placebo of identical appearance, for a period of 3 weeks. During the last week of the treatment period, BP was assessed at the morning and comparisons were made between placebo or melatonin treatments, and baseline. The results are shown in tables 2 and 3.

TABLE 2 results of Experiment 1

| | Systolic baseline | | Systolic Treatment | | | Diastolic baseline | | Diastolic Treatment | | |
|---|---|---|---|---|---|---|---|---|---|---|
| Dose | Average | SD | Average | SD | P value | Average | SD | Average | SD | P value |
| Hypertensive patients (>140 mm Hg Systolic BP at baseline) | | | | | | | | | | |
| 0 | 149 | 5 | 146 | 11 | 0.24 | 83 | 6 | 85 | 6 | 0.62 |
| 1 | 145 | 7 | 137 | 9 | 0.05 | 82 | 4 | 79 | 3 | 0.09 |
| 2 | 147 | 8 | 132 | 9 | 0.000009 | 81 | 6 | 76 | 6 | 0.0064 |
| 5 | 144 | 5 | 137 | 11 | 0.04 | 82 | 7 | 81 | 6 | 0.97 |
| Normotensive patients (<140 mm Hg Systolic BP at baseline) | | | | | | | | | | |
| 0 | 120 | 11 | 123 | 13 | 0.14 | 74 | 7 | 75 | 6 | 0.42 |
| 1 | 121 | 10 | 126 | 16 | 0.11 | 75 | 7 | 75 | 9 | 0.71 |
| 2 | 122 | 13 | 124 | 15 | 0.69 | 75 | 7 | 74 | 8 | 0.59 |
| 5 | 121 | 12 | 124 | 14 | 0.16 | 75 | 8 | 76 | 9 | 0.55 |

Conclusions

Exogenous melatonin administration in the evening decreased daytime systolic and diastolic in hypertensive elderly subjects. Surprisingly, the administration of the controlled release formulation (1-5 mg) had no significant effect in normotensive subjects. It may be noted that antihypertensive drugs cause a decrease in blood pressure when administered to normotensive subjects and that administration of a regular release formulation of melatonin (5 mg) in the evening has been shown to lower blood pressure in young normotensive subjects throughout the 24 h period. (Lusardi et al, Blood Press Monit 1997; 2: 99-103).

EXPERIMENT 2

Sixteen elderly patients with essential hypertension were studied. Twenty-four hour ambulatory blood pressures were measured in all patients. Patients were defined as dippers (n=8) or nondippers (n=8) according to nocturnal fall in mean arterial pressure. 24-hours urine was collected in two collections, one during daytime, and one during nighttime. Urinary excretion of the main melatonin metabolite 6-sulfatoxymelatonin (6SMT) was determined by ELISA assay in duplicates. Both groups were similar in regard to age and sex. Mean arterial pressure decreased by 10.2% during nighttime in the dippers and increased by 8% in the nondipper patients. Urinary 6SMT increased by 240% during sleep, from 3.28±0.87 (units) during daytime to 8.19±1.68 (units) during nighttime (p<0.05) in the dippers, whereas it remained unchanged in the nondippers (2.31±0.68 (units) during daytime and 2.56±0.79 (units) during nighttime). Results are shown in table 3.

TABLE 3 results of Experiment 2

|  | Dippers (n = 8) | Nondippers (n = 8) |
|---|---|---|
| Day | 3.28 ± 0.87 | 2.31 ± 0.68 |
| Night | 8.19 ± 1.68 | 2.56 ± 0.79 |

Conclusions

Nondipper hypertensive patients exhibit blunted nocturnal melatonin secretion. Thus, exogenous melatonin may play a role in the circadian rhythm of blood pressure.

Investigation of the Effect of Melatonin on Cortisol Profile and Mood

The following experiments were performed in a double-blind, placebo controlled crossover fashion. Each patient received all three kinds of tablets (placebo, regular release and controlled release) but in random order not known to him or the staff.

EXPERIMENT 3

Administration of melatonin (2 mg) in a controlled release formulation (SR-Mf), once daily at 10 PM, for one week, to eight healthy elderly persons suffering from insomnia, resulted in a significant increase in their sleep efficiency but not sleep latency. (Sleep efficiency is the amount of time spent asleep from total time in bed; sleep latency is the time taken to fall asleep from first lights-off). On the other hand treatment of the same individuals with melatonin (2 mg) in a regular release formulation (RM) did not improve sleep efficiency but shortened sleep latency compared to placebo treatment of the same subjects. These results can be explained by the short half-life of melatonin in the blood. Namely, the controlled release formulation produces lower blood levels of the hormone for extended periods of time and thus its effects may start slowly but may be significant later on during the night.

The cortisol level in these patients was assessed by the urinary excretion of the hormone at 2 hours intervals over a 24 hour period. In the placebo treatment group, patients displayed a cortisol rhythm which reached its peak at 8:36 μM and the cortisol then declined as is known for subjects above 40 years of age (see Sherman et al., Journal of Clinical Endocrinology and Metabolism 1985, 61: 439). The mean 24 hour excretion rate/hour (which approximated blood concentrations) of the cortisol in urine in the control group was 3.2 microgram/hour. The amplitude of the rhythm (i.e. maximal deviation of the mean 24 h to maximum or minimum excretion rate) was 1.8 μg/hour.

After treatment for 1 week with the regular release melatonin the overall amount of cortisol excreted was reduced The mean 24 hour excretion rate decreased to 2.5 μg/hour and the amplitude decreased to 1.0 μg/hour. In addition there was a slight backwards shift in the time of the peak, which occurred at 8:27 μM. Anticipation of the cortisol rhythm after administration of regular release melatonin is compatible with observations made by Terzolo at al., J Pineal Research, 1990, 9: 113-124. However, decrease in mean 24 hour levels and amplitude of the cortisol rhythm was not observed by Terzolo.

After one week's treatment with controlled release melatonin, it was found that like the regular melatonin, secretion of cortisol was attenuated (mean 24 h rate was 2.5 μg/hour) and the amplitude 1.2 μg/hour as with the regular release), but the peak was delayed significantly to later in the day and occurred at 12:06 PM. Thus, the peak was delayed by administration of controlled release melatonin instead of being the same or slightly advanced. The same cortisol profile was also found in these patients after 1 month's treatment with the controlled release formulation (mean 24 hour excretion 2.5 μg/hour, amplitude 1.0 μg/hour and peak time 12:08 hours).

Conclusions

These results show that the response of the body to melatonin is not obvious: the body reads the melatonin profile and not just the fact that it is present at some time. Interestingly, in humans younger than 40 years, the cortisol rhythm is also delayed compared to older individuals (Sherman et al., loc cit). Hence, the cortisol profile generated in the elderly after the controlled release melatonin treatment is similar to that in younger individuals.

Discussion

It has recently been found that in coronary patients, melatonin at night is low whereas cortisol levels are high (Brugger and Herold, Biological Rhythm Research, 1995, 26: 373). It should be noted that cortisol is a stress hormone, and its high levels in the morning may be linked to the increased prevalence of heart attacks in the morning hours. The present experiment shows that administration of regular release melatonin can lower cortisol production but that administration of controlled release melatonin both lowers the cortisol level and delays its peak and thus can potentially lower the risk for an ischemic attack during the morning hours.

EXPERIMENT 4

This experiment was performed on 10 young healthy males age 26-30. They received one controlled-release (SR-Mf) or regular release (RM) tablet containing melatonin (2 mg) or placebo per day with one day washout between treatments. The tablets were taken at 11:00 AM and the subjects were asked to sleep between 12-15 hours. Mood was assessed by Lader-Bond visual analog scale questionnaires before and after the sleep. The results indicated that regular melatonin (2 mg) significantly shortened nap sleep latency and increased sleep efficiency. The controlled release formulation also had similar effects. However, the regular release form produced feelings of hostility and sleepiness whereas the controlled release form had no negative effect on mood. These data also indicate that the effects of melatonin on mood depend on the profile generated. It should be noted that the lack of effect on mood cannot be explained by the lower concentrations of melatonin generated in the blood by the controlled release formulation since similar concentrations of melatonin (regular) have been shown by several studies to affect mood and sleepiness. Hence, both the timing and pattern of melatonin administration are important in affecting physiological parameters. The same dose given at different times or in different patterns may have different effects.

While particular embodiments of the invention have been particularly described hereinabove, it will be appreciated that the present invention is not limited thereto, since as will be readily apparent to skilled persons, many variations and modifications can be made. Such variations and modifications which have not been detailed herein are deemed to be obvious equivalents of the present invention. For example, structural analogs of melatonin which substantially imitate the function of melatonin in the human body are deemed to be obvious chemical equivalents of melatonin. The essential concept, spirit and scope of the present invention will be better understood in the light of the claims which follow.

The invention claimed is:

1. A method for the treatment of symptoms of hypertension in a patient who is suffering from hypertension and is resistant to antihypertensive effects of an antihypertensive compound administered in the absence of melatonin, which comprises administering to said patient melatonin in an amount effective to ameliorate symptoms of hypertension in said patient.

2. The method of claim 1, wherein said melatonin is administered as a pharmaceutical formulation which further comprises at least one carrier, diluent or adjuvant.

3. The method of claim 2, wherein said formulation is adapted for oral, rectal, parenteral or transdermal administration.

4. The method of claim 2 wherein said formulation is in unit dosage form, each unit dosage comprising an amount of melatonin within the range of 2.5-20 mg.

5. The method of claim 2 wherein said formulation is in the form of a controlled release formulation.

6. The method of claim 2, wherein said formulation further comprises at least one melatonin receptor modifier or melatonin profile modifier.

7. The method of claim 2, wherein said carrier, diluent or adjuvant in said formulation includes at least one acrylic resin.

8. The method of claim 1, wherein said patient is a non-dipper or exhibits a morning rise in blood pressure despite use of antihypertensive drugs.

* * * * *